(12) United States Patent
Kroll et al.

(10) Patent No.: US 7,225,020 B1
(45) Date of Patent: *May 29, 2007

(54) SYSTEM AND METHOD FOR PROVIDING PREVENTIVE OVERDRIVE PACING AND ANTITACHYCARDIA PACING USING AN IMPLANTABLE CARDIAC STIMULATION DEVICE

(75) Inventors: Mark W. Kroll, Simi Valley, CA (US); Eric Falkenberg, Simi Valley, CA (US); Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 387 days.

This patent is subject to a terminal disclaimer.

(21) Appl. No.: 10/657,963

(22) Filed: Sep. 8, 2003

(51) Int. Cl.
*A61N 1/05* (2006.01)
(52) U.S. Cl. .................. 607/14; 607/4; 607/5; 607/28; 600/515; 600/518
(58) Field of Classification Search .................. 607/14, 607/28, 4–5; 600/515, 518
See application file for complete search history.

(56) References Cited

U.S. PATENT DOCUMENTS

| | | | | |
|---|---|---|---|---|
| 4,686,988 | A | 8/1987 | Sholder | 128/419 |
| 4,787,389 | A | 11/1988 | Tarjan | 128/419 PG |
| 4,969,467 | A | 11/1990 | Callaghan et al. | 128/419 |
| 4,998,974 | A | 3/1991 | Aker | 128/419 |
| 5,109,842 | A | 5/1992 | Adinolfi | 128/419 |
| 5,243,978 | A | 9/1993 | Duffin, Jr. | 607/11 |
| 5,350,401 | A | 9/1994 | Levine | 607/4 |
| 5,350,410 | A | 9/1994 | Kleks et al. | 607/28 |
| 5,431,689 | A | 7/1995 | Weinberg et al. | 607/14 |
| 5,846,264 | A | 12/1998 | Andersson et al. | 607/28 |
| 5,861,008 | A | 1/1999 | Obel et al. | 607/11 |
| 5,978,709 | A | 11/1999 | Begemann et al. | 607/14 |
| 6,038,474 | A | 3/2000 | Zhu et al. | 607/9 |
| 6,058,328 | A * | 5/2000 | Levine et al. | 607/14 |
| 6,101,414 | A | 8/2000 | Kroll | 607/14 |
| 6,101,416 | A | 8/2000 | Sloman | 607/28 |
| 6,243,606 | B1 | 6/2001 | Mann et al. | 607/14 |
| 6,259,950 | B1 | 7/2001 | Mann et al. | 607/28 |
| 6,263,244 | B1 | 7/2001 | Mann et al. | 607/28 |
| 6,285,908 | B1 | 9/2001 | Mann et al. | 607/28 |
| 6,311,089 | B1 | 10/2001 | Mann et al. | 607/30 |
| 6,324,427 | B1 | 11/2001 | Florio | |

(Continued)

FOREIGN PATENT DOCUMENTS

EP   0436 517 B1   1/1991

*Primary Examiner*—Robert E. Pezzuto
*Assistant Examiner*—Deborah Malamud

(57) ABSTRACT

Techniques for enabling both preventive overdrive pacing and antitachycardia pacing (ATP) within an implantable device are provided. The device gains the benefits of overdrive pacing for preventing the onset of a tachycardia and, if one nevertheless occurs, ATP is employed to terminate the tachycardia. In particular, a technique is provided for promptly detecting the onset of atrial tachycardia during preventive overdrive pacing based on loss of capture of atrial pacing pulses. A technique is also provided for using detection of loss of capture of atrial or ventricular pacing pulses to trigger automatic switching from overdrive pacing to ATP. A setup technique determines whether to enable the automatic switching from overdrive pacing to ATP within a particular patient. Also, techniques are provided for verifying loss of capture of atrial or ventricular backup pacing pulses and for detecting low amplitude ventricular fibrillation based on loss of capture of ventricular backup pacing pulses.

19 Claims, 7 Drawing Sheets

U.S. PATENT DOCUMENTS

| | | | |
|---|---|---|---|
| 6,330,477 B1 | 12/2001 | Casavant | 607/14 |
| 6,345,201 B1 | 2/2002 | Sloman et al. | 607/28 |
| 6,430,441 B1 | 8/2002 | Levine | 607/28 |
| 6,434,428 B1 | 8/2002 | Sloman et al. | 607/28 |
| 6,456,881 B1 | 9/2002 | Bornzin et al. | 607/27 |
| 6,456,882 B1 | 9/2002 | Schloss | 607/28 |
| 6,512,953 B2 | 1/2003 | Florio et al. | 607/28 |
| 6,519,493 B1 | 2/2003 | Florio et al. | 607/9 |
| 6,522,925 B1 | 2/2003 | Glikerson et al. | 607/30 |
| 6,553,259 B2 | 4/2003 | Mouchawar et al. | 607/11 |
| 6,697,673 B1 | 2/2004 | Lu | 607/28 |
| 6,721,601 B1 | 4/2004 | Bornzin et al. | 607/28 |
| 6,731,978 B2 | 5/2004 | Olsson et al. | 607/4 |
| 6,829,504 B1 | 12/2004 | Chen et al. | 607/4 |
| 2001/0021036 A1 | 9/2001 | Sweeney et al. | 600/515 |
| 2003/0083703 A1 | 5/2003 | Zhu et al. | |
| 2003/0208241 A1* | 11/2003 | Bradley et al. | 607/27 |

* cited by examiner

SYSTEM AND METHOD FOR PROVIDING PREVENTIVE OVERDRIVE PACING AND ANTITACHYCARDIA PACING USING AN IMPLANTABLE CARDIAC STIMULATION DEVICE

CROSS-REFERENCE TO RELATED APPLICATIONS

This application is related to copending U.S. patent applications: 1) Ser. No. 10/657,858, titled "System and Method for Providing Preventive Overdrive Pacing and Antitachycardia Pacing Using an Implantable Cardiac Stimulation Device"; 2) Ser. No. 10/657,897, titled "System and Method for Providing Preventive Overdrive Pacing and Antitachycardia Pacing Using an Implantable Cardiac Stimulation Device"; 3) Ser. No. 10/657,840, titled "System and Method for Providing Preventive Overdrive Pacing and Antitachycardia Pacing Using an Implantable Cardiac Stimulation Device"; and 4) Ser. No. 10/657,878, titled "System and Method for Providing Preventive Overdrive Pacing and Antitachycardia Pacing Using an Implantable Cardiac Stimulation Device"; all applications filed concurrently herewith.

FIELD OF THE INVENTION

The invention generally relates to implantable cardiac stimulation devices such as pacemakers or implantable cardioverter defibrillators (ICDs), and, in particular, to techniques for overdrive pacing heart tissue to prevent tachycardia and for performing antitachycardia pacing to terminate tachycardia.

BACKGROUND OF THE INVENTION

An arrhythmia is an abnormal heart beat pattern. One example of arrhythmia is bradycardia wherein the heart beats at an abnormally slow rate or wherein significant pauses occur between consecutive beats. Other examples of arrhythmias include tachyarrhythmias wherein the heart beats at an abnormally fast rate. With atrial tachycardia, the atria of the heart beat abnormally fast. With ventricular tachycardia, the ventricles of the heart beat abnormally fast. Though often unpleasant for the patient, a tachycardia is typically not fatal. However, some types of tachycardia, particularly ventricular tachycardia, can trigger ventricular fibrillation wherein the heart beats chaotically such that there is little or no net flow of blood from the heart to the brain and other organs. Ventricular fibrillation, if not terminated within minutes, is fatal. Hence, it is highly desirable to prevent or terminate arrhythmias, particularly arrhythmias of the type that can lead to a ventricular fibrillation.

One technique for preventing tachycardias is to pace the heart at a rate somewhat faster than the intrinsic heart rate of the patient using a technique referred to as overdrive pacing. To help prevent a tachycardia from occurring, the stimulation device artificially paces the heart at an overdrive rate set to be slightly faster than the intrinsic heart rate of the patient. One particularly effective overdrive pacing technique, referred to herein as dynamic atrial overdrive (DAO) pacing, is described in U.S. Pat. No. 6,519,493 to Florio et al., entitled "Methods And Apparatus For Overdrive Pacing Heart Tissue Using An Implantable Cardiac Stimulation Device," which is incorporated by reference herein. With DAO, the overdrive rate is controlled to remain generally uniform and, in the absence of a tachycardia, is adjusted upwardly or downwardly only occasionally. Dynamic overdrive techniques are also applicable to the ventricles and exemplary dynamic ventricular overdrive (DVO) techniques are described in U.S. patent applications: 1) Ser. No. 10/456,060 to Park et al., entitled "System And Method For Dynamic Ventricular Overdrive Pacing," filed Jun. 6, 2003; and 2) Ser. No. 10/456,058, entitled "System And Method For Dynamic Ventricular Overdrive Pacing," Jun. 6, 2003, which applications are also incorporated herein by reference.

It is believed that DAO and DVO are effective for at least some patients for preventing tachycardia for the following reasons. A normal, healthy heart typically beats only in response to electrical pulses generated from a portion of the heart referred to as the sinus node. The sinus node pulses are conducted to the various atria and ventricles of the heart via certain, normal conduction pathways. In some patients, however, additional portions of the heart also generate electrical pulses referred to as "ectopic" pulses. Each pulse, whether a sinus node pulse or an ectopic pulse has a refractory period subsequent thereto during which time the heart tissue is not responsive to any electrical pulses. A combination of sinus pulses and ectopic pulses can result in a dispersion of the refractory periods, which, in turn, can trigger a tachycardia. By overdrive pacing the heart at a generally uniform rate slightly above the intrinsic rate, the likelihood of the occurrence of ectopic pulses is reduced and the refractory periods within the heart tissue are rendered more uniform and periodic. Thus, the dispersion of refractory periods is reduced and the risk of tachycardia is reduced. Thus, overdrive pacing, particularly DAO and DVO, provides a useful technique for helping to prevent the onset of a tachycardia and for terminating a tachycardia should one nevertheless arise. Utilizing an overdrive algorithm in conjunction with multisite stimulation will also result in a collision of the electrical wavefronts further reducing dispersion of the refractory period effectively reducing the risk of tachycardia.

Herein, the term "overdrive pacing" generally refers to the sustained pacing of chambers of the heart at a rate higher than the intrinsic rate. Overdrive pacing can take the form of "preventive overdrive pacing", which is employed for the purposes of preventing a tachycardia from occurring, and "therapeutic overdrive pacing", which is employed for the purposes of terminating a tachycardia should one nevertheless arise. The overdrive rates associated with preventive overdrive pacing are much lower than those associated with therapeutic overdriving pacing.

Therapeutic overdrive pacing represents one type of antitachycardia pacing (ATP). Other ATP techniques have been developed as well that do not exploit overdrive pacing or at least do not exploit sustained overdrive pacing. The underlying principle of many such techniques is that if an implantable stimulation device delivers a stimulation pulse to the heart during a critical time period following a naturally occurring heartbeat during tachycardia, the tachycardia pathway will be rendered refractory abruptly terminating the tachycardia allowing the heart to revert to sinus, or natural, rhythm. In this regard, certain types of tachycardias are the result of an electrical feedback mechanism within the heart. For example, a natural heartbeat can occur through a normal pathway and re-enter through an alternate loop of tissue that perpetuates conduction (also known as an accessory or re-entrant pathway), thereby initiating a tachycardia. The delivery of a stimulation pulse causes the cardiac tissue in front of the stimulation pulse to depolarize (thereby causing the heart to contract), but leaves the tissue at the stimulation site refractory (i.e., the tissue cannot respond to additional stimulation). Thus, by injecting a stimulation pulse within the cardiac cycle, the stability of the feedback loop is disrupted and the tachycardia terminated thus allowing the heart may revert to a natural sinus rhythm.

One example is burst pacing (or "shotgunning") wherein several sequential, rapid stimuli are delivered to the heart in an effort to terminate the tachycardia. The theory behind providing a burst of pulses is that sooner or later one of the stimulating pulses will occur at a time in the tachycardia cycle which will terminate the tachycardia (i.e. the pulse will occur during a "region of susceptibility"). Burst pacing may be delivered asynchronously or synchronously at a fixed, decreasing, or increasing, cycle length from a tachycardia complex until the tachycardia is terminated. Once the tachycardia has been terminated, the timing associated with the burst that succeeded in terminating the tachycardia may be stored and used as the starting point for applying a new burst of simulation pulses to the heart upon the next occurrence of a tachycardia. An alternate technique to find the termination window is by "scanning", which is a type of burst pacing with variations in coupling interval. This technique utilizes an implantable stimulation device that automatically searches or "scans" for the pacing interval most likely to terminate a tachycardia. The implantable stimulation device delivers single or multiple stimulation pulses at "critically timed" coupling intervals and continues in a controlled sequence until the tachycardia terminates. For example, the controlled sequence may begin with a single stimulation pulse at one end of the scanning window and, with each successive tachycardia cycle, deliver additional pulses at increasing (or decreasing) coupling intervals in a controlled manner towards the other end of the window. Hence, the stimulation pulse scans through the scanning window looking for the region of susceptibility.

Exemplary patents describing ATP techniques include U.S. Pat. No. 6,101,414, to Mark Kroll, entitled "Method And Apparatus For Antitachycardia Pacing With An Optimal Coupling Interval," and U.S. Pat. No. 5,431,689 to Weinberg et al., entitled "Implantable Stimulation System And Method For Terminating Cardiac Arrhythmias," which are both incorporated by reference herein.

Regardless of the specific ATP technique, it has been found that ATP is most effective if applied early during the tachycardia. Unfortunately, conventional techniques for detecting the onset of a tachycardia do not detect the tachycardia as promptly as would be desired. One technique for detecting an atrial tachycardia is to monitor the atrial rate and initiate atrial ATP if the heart rate exceeds a certain threshold, typically referred to as an atrial tachycardia detection rate (ATDR). It may take a fair number of cardiac cycles, however, before the stimulation device can reliably detect a high atrial rate and, in particular, distinguish a high heart rate from a temporary shortening of an atrial heart rate interval caused by a premature beat such as a premature atrial contraction (PAC). It is also known to try to differentiate pathologic rhythms from normal physiologic rhythms by analyzing heart rate stability. Again, though, a fair number of cycles may be required before the stimulation device can reliably distinguish a change in heart rate stability caused by a tachycardia from one caused by premature beats or other transient factors. Conventional techniques for detecting a tachycardia are discussed in U.S. Pat. No. 5,109,842, to Adinolfi, entitled "Implantable Tachyarrhythmia Control System Having a Patch Electrode with an Integrated Cardiac Activity System."

Also, care must be taken to ensure that ATP is not erroneously activated in circumstances where it is not needed and, in particular, in circumstances where it might be proarrhythmic. In this regard, in some patients, there are a large number of short nonsustained salvos of supraventricular tachycardia (SVT) or multiple sequential PACs which, if they occur during a post-ventricular atrial refractory period (PVARP), will not inhibit the atrial output thereby causing the atrial output to be delivered to a period of physiologic refractoriness in the atrial myocardium. Indeed, delivering a burst of ATP into a rhythm that would not have been sustained may be arrhythmogenic inducing atrial flutter or atrial fibrillation (AF) where this would not have occurred spontaneously. The need to avoid erroneous triggering of ATP often means that the tachycardia detection technique must process even more data before reliably concluding that a tachycardia has occurred.

Similar problems can arise in the detection of certain ventricular tachycardias. Failure to promptly detect a ventricular tachycardia (such as a low amplitude ventricular fibrillation (VF)) can result in a delay in the delivery of defibrillation shocks with a reduced likelihood of success. In this regard, it has been proposed to use the detection of loss of capture (LOC) of a series of ventricular pacing pulses as a means for detecting low amplitude VF and for triggering delivery of a high output defibrillation shock. See U.S. Pat. No. 5,350,401 to Levine, which is incorporated herein by reference. With that technique, upon detection of loss of capture of a ventricular pulse, the ventricular pulse output magnitude is increased and another pulse is delivered. If that pulse also fails to capture, the output magnitude is increased again. This process proceeds until either a ventricular pulse captures or until a maximum pulse output level is reached. If the maximum output is reached and the ventricular pulses still do not evoke capture, a determination is thereby made that a low amplitude VF may have occurred and a defibrillation shock may be delivered to terminate the VF. Although the technique is effective in eventually detecting low amplitude VF, the need to deliver a series of ventricular pulses with different pulse magnitudes delays the detection of VF, thus potentially reducing the effectiveness of subsequent shock therapy.

Thus, conventional atrial and ventricular tachycardia detection techniques do not always detect tachycardia as quickly as desired, resulting in a reduced likelihood that subsequent therapy will be successful. Accordingly, it would be desirable to provide improved techniques for promptly and reliably detecting atrial and ventricular tachycardias and aspects of the invention are generally directed to these ends. In particular, it would be desirable to provide techniques for exploiting the detection of loss of capture of backup pacing pulses in the detection of tachycardia. As will be explained below, loss of capture of backup pulses can be used to promptly detect a tachycardia.

The aforementioned problems associated with promptly detecting a tachycardia are even more problematic if preventive overdrive pacing were also to be performed. For example, in the technique where ATP is triggered based on intrinsic atrial rate, routine preventive overdrive pacing would prevent the device from continuously and reliably monitoring the intrinsic atrial rate. Using DAO, for example, the intrinsic atrial rate is not evaluated at all. Rather, increases or decreases in the overdrive rate are made based solely on the presence or absence of breakthrough beats. Alternatively, ATP could be triggered once the preventive overdrive pacing rate itself exceeds the ATDR, but it may take too many cycles before the overdrive rate is boosted up to that threshold. Also, as typically implemented, preventive atrial overdrive pacing rates never exceed the ATDR because the pacing device is programmed to never exceed a maximum overdrive rate that is set well below the ATDR. Likewise, techniques based on heart rate stability are not easily and effectively implemented during preventive overdrive pacing.

For these and other reasons, most conventional pacing devices do not provide for both preventive overdrive pacing and ATP. In devices that do provide for both (see, for example, the AT500 pacemaker provided by Medtronic Corporation of Minneapolis, Minn., USA), it does not appear that ATP is triggered as promptly as desired and so may not provide optimal termination of the tachycardia. Accordingly, it also would be desirable to provide improved techniques promptly switching from preventive overdrive pacing to ATP and additional aspects of the invention are directed to these ends.

In view of the risks associated with delivering ATP during arrhythmias that otherwise would not be sustained (such as where burst ATP might actually induce atrial flutter or fibrillation), it also would be desirable to provide techniques for determining whether to enable automatic switching of preventive overdrive pacing to ATP within a particular patient and still other aspects of the invention are directed to that end.

SUMMARY OF THE INVENTION

In accordance with a first aspect of the invention, systems and methods are provided for use with implantable cardiac stimulation devices for promptly and reliably detecting the onset of an atrial tachycardia. In one embodiment, wherein the stimulation device includes a pacing unit and an atrial pulse capture detection unit, pacing pulses are delivered to the atria using the pacing unit and atrial tachycardia is detected based on the loss of capture of the atrial pacing pulses. By detecting atrial tachycardia based on loss of capture of atrial pacing pulses, rather than other, slower techniques, atrial tachycardia can be promptly detected, thereby permitting ATP to be delivered as early as possible within the episode of atrial tachycardia to provide the best possible chance of success.

In one specific example, wherein atrial pacing pulses are delivered at a maximum pulse magnitude, atrial tachycardia is detected by identifying loss of capture of a single one of the atrial pacing pulses or by instead detecting loss of capture of both a primary pulse and a backup pulse, both delivered at the maximum magnitude. If primary pacing pulses are instead delivered at a pulse magnitude less than a maximum pulse magnitude, atrial tachycardia is detected by identifying loss of capture of both a primary pacing pulse and a subsequent backup pacing pulse delivered at the maximum pulse magnitude. Alternatively, rather than predicating the detection of atrial tachycardia on a LOC of a single primary pacing pulse or on a LOC of a pacing pulse/backup pulse pair, atrial tachycardia can instead be detected by identifying some number of LOCs out of a predetermined number of pulses or pulse pairs (i.e. by detecting "x" LOCs out of the last "y" pulses). This helps prevent any coincidental LOC due to a short salvo of rapid ventricular rates from resulting in the erroneous detection of an atrial tachycardia. Also, in implementations wherein pacing pulses are delivered at a pulse magnitude less than a maximum pulse magnitude, the stimulation device preferably includes an automatic stimulation threshold search unit operative to determine a capture threshold for setting the magnitude of the primary (i.e. non-backup) atrial pacing pulses. The magnitudes of the primary pulses are set to a working margin just above the determined capture threshold. The threshold search is automatically performed whenever the primary pacing pulse is not captured on two consecutive complexes but where the back-up pulses are captured. Threshold searches may be performed periodically as well.

In accordance with a second aspect of the invention, systems and methods are provided for use with implantable cardiac stimulation devices for providing both preventive overdrive pacing therapy and ATP therapy. In one embodiment, the stimulation device includes a preventive overdrive pacing unit operative to deliver overdrive pacing pulses to the heart, an ATP therapy unit operative to deliver antitachycardia pacing therapy to the heart and a tachycardia detection unit operative to detect tachycardia. A control unit is provided that is operative to switch from preventive overdrive pacing to ATP upon detection of a tachycardia. By providing for both preventive overdrive pacing and ATP within a stimulation device, the likelihood of onset of a tachycardia can be reduced by overdrive pacing but, if one should nevertheless occur, ATP can be use to terminate the tachycardia. Preferably, tachycardias are detected based on the loss of capture of pacing pulses in accordance with the first aspect of the invention, such that ATP can be promptly activated to have the best likelihood of success. In one specific example, the stimulation device also includes a PAC detection unit for detecting PACs during preventive overdrive pacing and the control unit is also operative to switch from preventive overdrive pacing and to ATP upon the detection of a loss of capture of a backup pulse delivered subsequent to detection of a PAC during preventive overdrive pacing.

In accordance with a third aspect of the invention, systems and methods are provided for use with implantable cardiac stimulation devices for determining whether to enable automatic switching from preventive overdrive pacing to ATP within a particular patient. In one embodiment, wherein the stimulation device includes an overdrive pacing unit, a tachycardia detection unit, an ATP therapy unit, and a capture detection unit, a setup technique is performed wherein preventive overdrive pacing is delivered to the heart and any loss of capture of pacing pulses is detected. Any tachycardias occurring subsequent to a loss of capture are detected using the tachycardia detection unit and a determination is made, for each such tachycardia, whether the tachycardia spontaneously terminates. Then, automatic switching from preventive overdrive pacing to ATP therapy is selectively enabled based on a percentage of spontaneously terminating episodes of tachycardia occurring subsequent to loss capture during preventive overdrive pacing.

Preferably, the percentage of spontaneously terminating episodes of tachycardia is compared against a predetermined threshold (such as 60%) and automatic switching from preventive overdrive pacing to ATP therapy is enabled only if the percentage does not exceed the predetermined threshold and is disabled otherwise. In this manner, loss of capture of overdrive pulses is only used to trigger an automatic switch from preventive overdrive pacing to ATP within those patients in which most tachycardias arising subsequent to a loss of capture do not spontaneously terminate. In patients in which such tachycardias do indeed spontaneously terminate, switching from preventive overdrive pacing to ATP is not enabled, at least based on loss of capture. This minimizes the delivery of ATP to patients for whom it is not necessary and could be arrhythmogenic. In one specific example, the setup technique is performed for a predetermined period of time, for example one to two months, following implant of the stimulation device within the patient to permit a reliable determination to be made as the percentage of tachycardia episodes that spontaneously terminating following loss of capture. Alternatively, the setup technique is performed until a predetermined number of tachycardia episodes are detected. In either case, the setup technique is preferably repeated periodically to account for any changes in the percentage of tachycardia episodes that spontaneously terminate within the patient.

In accordance with a fourth aspect of the invention, capture verification is applied to backup pacing pulses, whether in the atria or ventricles. An implantable cardiac stimulation device is provided, which includes a pacing unit for delivering primary pacing pulses to the heart, a pulse capture detection unit operative to detect loss of capture of primary pacing pulses, and a backup pulse unit for delivering backup pulses to the heart upon detection of a loss of capture of a primary pacing pulse. The capture detection unit is further operative to detect loss of capture of the backup pacing pulses. As noted above, detection of loss of capture of backup pulses in the atria may be used as a basis for detecting an atrial tachycardia and for triggering ATP. Detection of loss of capture of backup pulses may be used in other circumstances as well, such as for the detection of low amplitude VF based on loss of capture of ventricular backup pulses.

In accordance with a fifth aspect of the invention, loss of capture of backup pacing pulses in the ventricles is used to detect ventricular tachycardia, particularly low amplitude VF. Briefly, an implantable cardiac stimulation device is provided, which includes a pacing unit operative to deliver primary pacing pulses and backup pacing pulses to the ventricles of the heart and a capture detection unit operative to detect loss of capture of both primary pacing pulses and backup pacing pulses in the ventricles. A capture-based ventricular tachycardia detection unit is also provided, which is operative to detect a ventricular tachycardia based upon loss of capture of a ventricular backup pulse as detected by the capture detection unit.

Thus, a variety of techniques are provided for promptly detecting atrial and ventricular tachycardias and for enabling use of both preventive overdrive pacing and ATP within implantable stimulation devices. Other features, advantages and objectives of the invention will be apparent from the accompanying drawings in connection with descriptions provided herein.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Device

Figure 1:
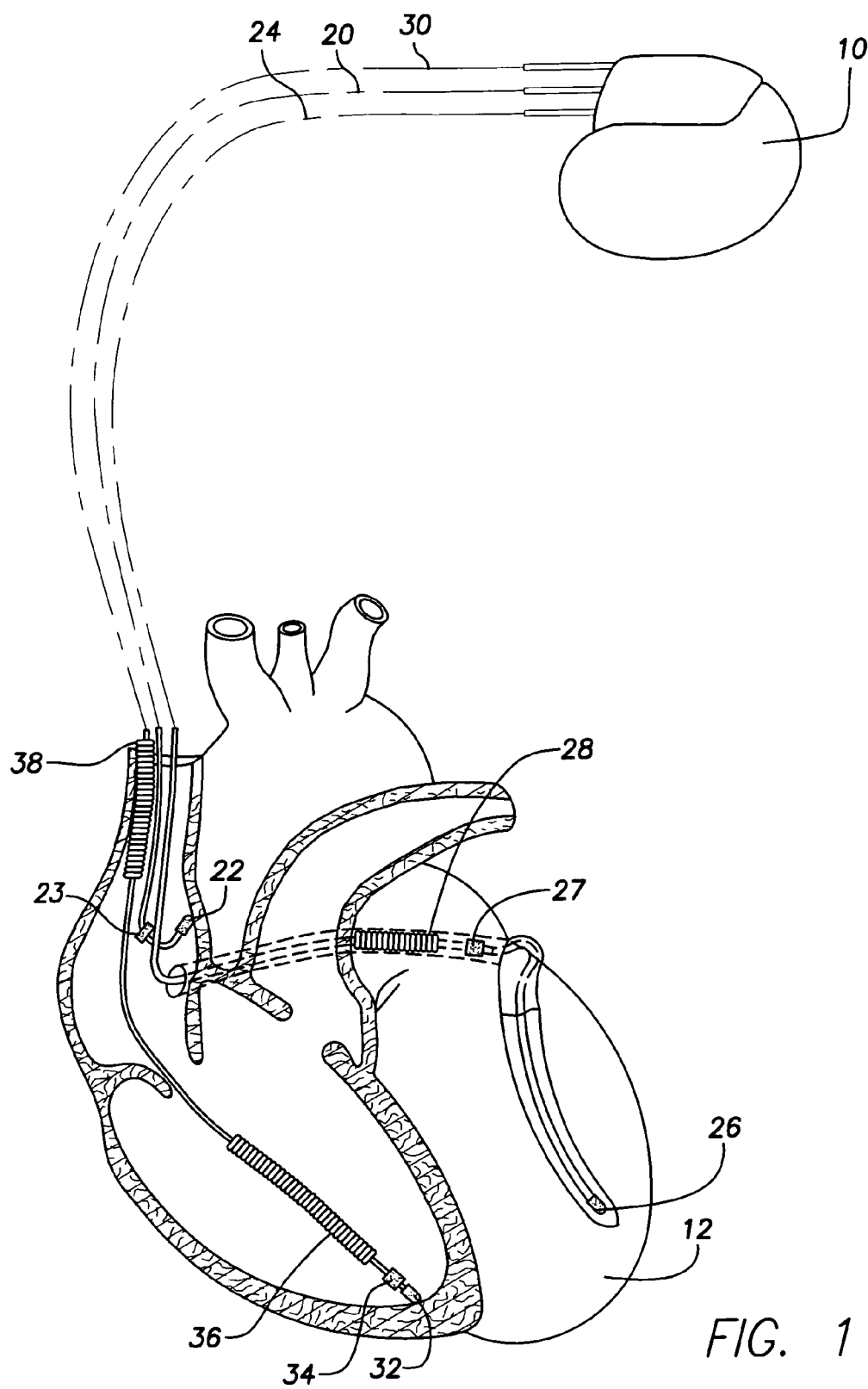
FIG. 1 is a simplified diagram illustrating an implantable stimulation device in electrical communication with at least three leads implanted into the heart of a patient for delivering multi-chamber stimulation and shock therapy and configured in accordance with the invention to perform preventive overdrive pacing and ATP.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage, and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
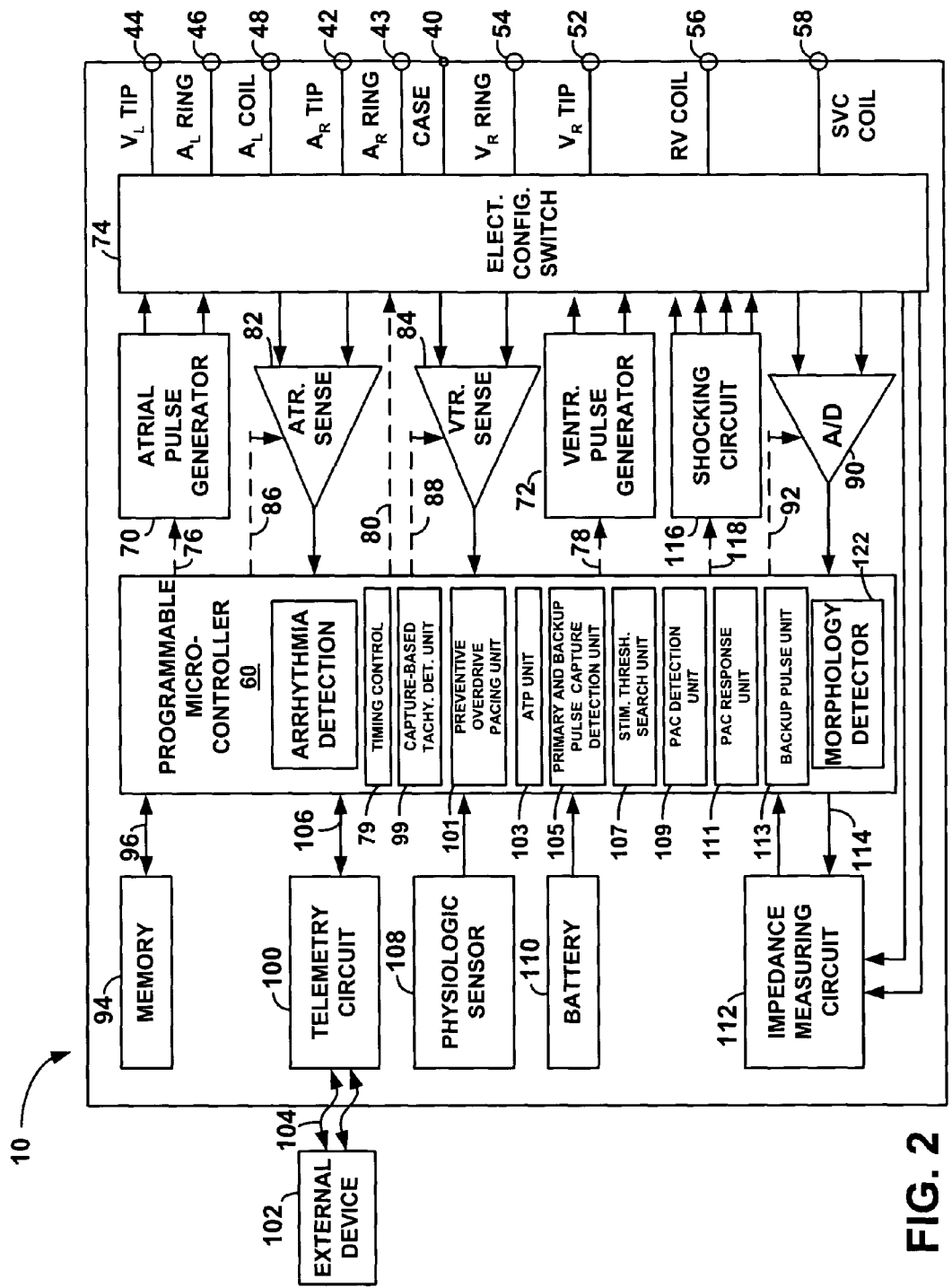
FIG. 2 is a functional block diagram of the implantable cardiac stimulation device of FIG. 1 illustrating basic elements of a stimulation device.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 and a right atrial ring ($A_R$ RING) electrode 43 adapted for connection to right atrial ring electrode 23. To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art. Switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy"). Similar capabilities would exist on the atrial channel with respect to tachycardias occurring in the atrium. These would be atrial tachycardias (AT), more rapid atrial tachycardias (Atrial Flutter) and atrial fibrillation (AF).

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller includes a capture-based tachycardia detection unit 99, which operates to detect a tachycardia based on loss of capture of pacing pulses. In the primary example described herein, the tachycardia detection unit operates to detect AF based on loss of capture of atrial pacing signals during preventive overdrive pacing in the atrium. Accordingly, the capture-based tachycardia detection unit is used in conjunction with a preventive overdrive pacing unit 101 for controlling overdrive pacing of the heart. The overdrive pacing unit preferably performs preventive overdrive pacing in accordance with the DAO technique described above in the Background of the Invention section and set forth in the above-cited patent Florio et al. In one example, the overdrive pacing unit operates continuously in the absence of a tachycardia so as to reduce the likelihood of the onset of a tachycardia. In other examples, preventive overdrive pacing is suspended while the patient is asleep. It is also suspended when the patient is in a tachycardia that has resulted in the enabling of the Automatic Mode Switch algorithm. In any case, if a tachycardia is detected during preventive overdrive pacing by the tachycardia detection unit, an ATP unit 103 is activated to deliver antitachycardia pacing to the heart in an effort to terminate the tachycardia. The ATP unit may administer ATP in accordance with any of a variety of ATP techniques, such as the techniques described in the Kroll and Weinberg patents cited above. As will be descried in greater detail below in connection with FIG. 3 and following, tachycardia may be detected during preventive overdrive pacing based, for example, upon detection of a true loss of capture of an preventive overdrive pacing pulse or upon detection of a loss of capture of a backup pulse subsequent to a PAC.

To detect loss of capture, the microcontroller also includes an automatic capture detection unit 105 for detecting an evoked response from the heart in response to an applied stimulus. As will be explained below, the capture detection unit verifies capture of both primary pacing pulses and any subsequent backup pulses. Capture occurs when an electrical stimulus applied to the heart is of sufficient energy to depolarize the cardiac tissue, thereby causing the heart muscle to contract. The capture detection unit detects a depolarization signal during a window following a stimulation pulse, the presence of which indicates that capture has occurred. Capture detection is performed on a beat-by-beat basis. If a primary pulse is not captured, a backup pulse unit 113 delivers a backup pulse at a maximum pulse magnitude. The capture detection unit also detects whether the backup pulse captures.

Also included is a stimulation threshold search unit 107 for automatically determining the current capture threshold of the patient, i.e. the minimum output sufficient to evoke capture, so that the output or pulse magnitude can be reset properly. This is commonly reported in terms of pulse amplitude as this is one of the programmable output parameters. As will be explained below, while preventive overdrive pacing is performed, is stimulation search is automatically performed in circumstances wherein a primary pacing pulse is not captured but the backup pulse is captured. (If both the overdrive pulse and the backup pulse are not captured, ATP is instead activated.) Also, preferably, a capture threshold search is performed periodically to update the capture threshold regardless of whether any loss of capture is detected. Such capture threshold searches are preferably performed every eight hours. Typically, a capture threshold search begins at a desired starting point (either a high energy level or the level at which capture is currently occurring) and decreases the energy level until capture is lost. It then increments the output in 0.125 Volt steps until capture is restored. The value at which capture is restored is known as the capture threshold. Thereafter, a working margin or a safety margin is added to the capture threshold to yield a new pulse magnitude. A safety margin is a fixed multiple of the measured threshold. A working margin is a fixed value, e.g. 0.25 Volts above the measured threshold. In the preferred implementation, the safety margin is provided by the high output backup pulse. The delivered output associated with the primary pulse is simply a working margin above the measured capture threshold.

Various techniques for implementing capture verification of atrial pacing pulses (i.e. atrial AutoCapture) are set forth in U.S. Pat. No. 6,434,428 to Sloman et al.; U.S. Pat. No. 6,311,089 to Mann et al.; U.S. Pat. No. 6,285,908 to Mann et al.; U.S. Pat. No. 6,263,244 to Mann et al.; U.S. Pat. No. 6,259,950 to Mann et al.; U.S. Pat. No. 6,243,606 to Mann et al.; and U.S. Pat. No. 6,101,416 to Sloman, which are incorporated herein by reference. Capture verification of ventricular pulses is described in U.S. Pat. No. 6,456,882 to Schloss; U.S. Pat. No. 6,456,881 to Bornzin et al.; and U.S. Pat. No. 6,345,201 to Sloman, et al, which are also incorporated herein by reference. See also U.S. Pat. No. 4,686,988 (Sholder); U.S. Pat. No. 4,969,467 (Callaghan et al.); and U.S. Pat. No. 5,350,410 (Mann et al.), which patents are hereby incorporated herein by reference. A technique for implementing automatic capture verification during overdrive pacing is described in U.S. patent application Ser. No. 10/138,438, filed May 2, 2002, of Bradley et al., entitled "Method And Apparatus For Providing Atrial Autocapture In A Dynamic Atrial Overdrive Pacing System For Use In An Implantable Cardiac Stimulation Device," which is incorporated herein by reference.

The microcontroller also includes a PAC detection unit 109 and a PAC response unit 111. The PAC detection unit detects PACs (in accordance with a technique described below in connection with FIG. 3 and following) and the PAC response unit provides a pacing protocol for responding to the PAC. An exemplary PAC response protocol is described in U.S. Pat. No. 5,978,709 to Begemann et al., entitled "Pacemaker System with Improved Techniques for Preventing and Suppressing Atrial Arrhythmias," which is incorporated herein by reference.

Although shown as being components of the microcontroller, any or all of capture-based tachycardia detection unit 99, overdrive pacing unit 101, ATP unit 103, capture detection unit 105, stimulation threshold search unit 107, PAC detection unit 109, PAC response unit 111, and backup pulse unit could be instead implemented as separate components. Also, depending up on the particular component and the particular implementation, individual components may be configured to apply to the ventricles, the atria, or in some cases both.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. (V—V delay is typically used in only connection with independently programmable RV and LV leads for biventricular pacing.) While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient.

The stimulation device additionally includes a battery 110, which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices. As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate antitachycardia pacing therapy or electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are of relatively low to moderate energy level (so as to minimize the current drain on the battery) and are usually between 5 to 20 joules. Typically, cardioversion shocks are synchronized with an R-wave. Defibrillation shocks are generally of moderate to high energy level (i.e., corresponding to thresholds in the range of 15 to 40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Referring to the remaining figures, flow charts are shown describing an overview of the operation and novel features of stimulation device 10 as configured in accordance with exemplary embodiments of the invention. In these flow charts, the various algorithmic steps are summarized in individual "blocks". Such blocks describe specific actions or decisions made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

Capture-Based Atrial Tachycardia Detection

Figure 3:
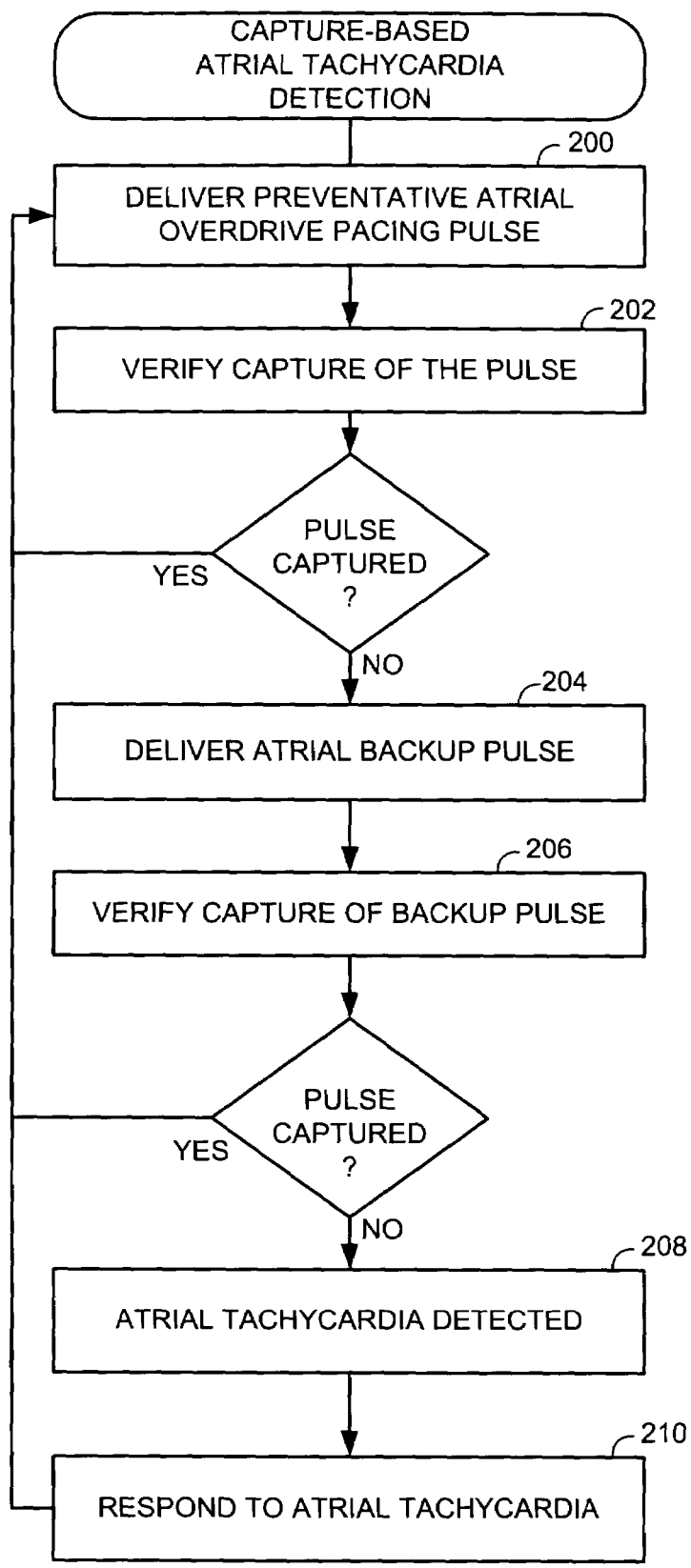
FIG. 3 is a flow chart providing an overview of the operation of an exemplary embodiment of the invention particularly illustrating the manner by which the implantable stimulation device of FIGS. 1 and 2 detects an atrial tachycardia based upon loss of capture of pacing pulses.

FIG. 3 provides an overview of a method performed by the capture-based tachycardia detection unit (item 99 of FIG. 2) for automatically detecting atrial tachycardia based on a loss of capture of atrial pacing pulses during preventive overdrive pacing. Initially, at step 200, the overdrive pacing unit (item 101 of FIG. 2) controls the delivery of preventive overdrive pacing to the heart and, at step 202, attempts to verify capture of each overdrive pulse using the capture detection unit (item 105 of FIG. 2), which is configured to verify capture of the atrial overdrive pacing pulses. So long as each pulse is captured, preventive atrial overdrive pacing is performed continuously via steps 200 and 202. If a pulse fails to capture (i.e. an LOC occurs), the LOC may be the result of the onset of an atrial tachycardia. More specifically, the sudden increase in atrial rate due to the tachycardia may have caused the atria to beat before the overdrive pulse could be delivered, rendering atrial tissue refractory at the time the overdrive pulse was delivered. Hence, the overdrive pulse is not captured and a LOC is detected. On the other hand, the LOC may be merely the result of the overdrive pulse having a magnitude set too low to properly evoke a depolarization response. So, at step 204, the stimulation device delivers an atrial backup pulse at a higher pulse magnitude and, at step, 206, attempts to verify capture of the backup pulse (again using the capture detection unit). If the backup pulse also fails to evoke a response, atrial tachycardia is thereby detected at step 208 and appropriate steps are taken at step 210 to respond to the atrial tachycardia.

Thus, FIG. 3 illustrates a technique wherein the detection of LOCs during preventive overdrive pacing is exploited to detect an atrial tachycardia. If the preventive overdrive pacing technique being employed is DAO, the atrial tachycardia detected is either an organized atrial tachycardia (AT) or AF and, accordingly, the response provided at step 210 is preferably directed to terminating the AT or AF, such as delivering atrial ATP. If ATP is ineffective, then atrial cardioversion shocks are utilized. In any case, with this technique, atrial tachycardia can be detected promptly so that responsive therapies have the maximum likelihood of success. At least insofar as AF is concerned, with many conventional AF detection techniques, by the time AF is detected and ATP is activated it may be too late to reliably terminate the AF.

Although not shown in FIG. 3, if the preventive overdrive pacing pulses delivered at step 200 are delivered at a maximum pulse magnitude, it may not be necessary to deliver a backup pulse at step 204. Rather, the loss of capture of the primary overdrive pulse may be sufficient to warrant the conclusion that a tachycardia has commenced. However, it may still be desirable to deliver a backup pulse anyway to thereby verify that the loss of capture of the primary pulse was indeed the result of a tachycardia.

Automatic DAO/ATP Switching Method

Figure 4:
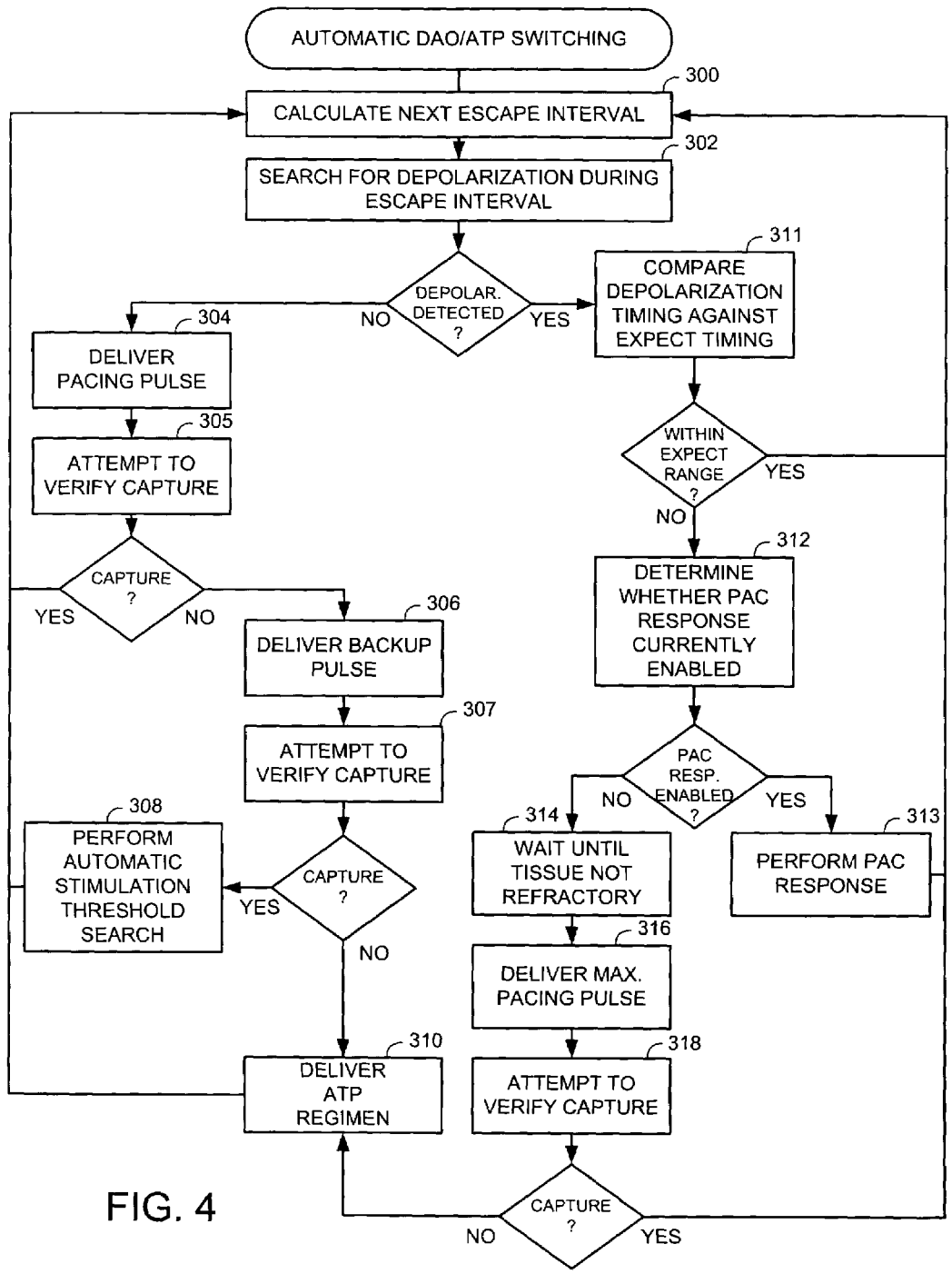
FIG. 4 is a flow chart providing an overview of the operation of another exemplary embodiment of the invention and particularly illustrating the manner by which the implantable stimulation device of FIGS. 1 and 2 automatically switches from preventive atrial overdrive pacing to ATP at the onset of an atrial tachycardia.

FIG. 4 illustrates an exemplary technique for automatically switching between preventive atrial overdrive pacing and therapeutic ATP upon detection of AF, which particularly highlights techniques for determining whether or not a LOC detected during preventive overdrive pacing is the result of AF. FIG. 4 assumes that preventive overdrive pacing has already been activated (preferably employing DAO techniques) and is on-going and that the pulse magnitude for overdrive pacing pulses has already been set based on a previous automatic stimulation threshold search performed by the capture detection unit (item 105 of FIG. 2). The pulse magnitude that is set via an automatic stimulation threshold search is typically substantially less than the maximum pulse magnitude that the stimulation device can deliver. In any case, while preventive overdrive pacing is performed in accord with the DAO algorithm, the overdrive pacing unit (item 101 of FIG. 2) calculates an escape interval for use in determining the time window to deliver a next overdrive pacing pulse. During step 302, the device waits during the escape interval to determine whether a depolarization occurs. If no depolarization is detected during the escape interval, the next overdrive pacing pulse is delivered at step 304. The automatic capture unit then attempts, at step 305, to verify that the overdrive pulse was properly captured and, if so, processing simply returns to step 300 for calculation of the next escape interval for delivery of the next pulse. However, if the overdrive pacing pulse of step 304 is not captured, a backup pulse is then delivered at step 306 by the overdrive pacing unit. The backup pulse is preferably set to a magnitude considerably greater then the magnitude of the overdrive pacing pulse of step 304. Depending upon the implementation, the back-up pulse may be set to the maximum pulse magnitude the stimulation device can deliver or to some magnitude intermediate the magnitude of the overdrive pacing pulse of step 304 and the maximum pulse magnitude. Also, in circumstances wherein the primary pulse is already at the maximum magnitude, a backup pulse may nevertheless be provided, also at the maximum magnitude.

At step 307, the capture detection unit again seeks to verify capture. If the previous overdrive pacing pulse of step 304 failed to evoke capture but the backup pulse of step 306 was properly captured, then the LOC associated with the overdrive pacing pulse was probably not the result of a AF but was instead probably the result of the overdrive pulse magnitude being set too low. Accordingly, at step 308, another automatic stimulation threshold search is performed (by the automatic capture unit) for the purposes of determining the new atrial capture threshold for the patient so that the magnitude of the overdrive pacing pulses can be set properly. However, if even the backup pulse of step 306 failed to properly evoke capture, then the heart is most likely suffering AT or AF and an ATP regimen is immediately initiated at step 310 using the ATP unit (item 103 of FIG. 2). In this manner, ATP is immediately activated upon the detection of an apparent AF so as to have the best possible chance of terminating AF. The ATP unit may be configured to perform any of a variety of ATP techniques, such as burst pacing or scanning ATP or therapeutic overdrive ATP. Once the ATP regimen is complete, processing returns to step 300 for calculation of the next escape interval. Note that, if the ATP regimen is not successful, another LOC of a backup pulse will likely be detected again and another ATP regimen promptly delivered. Additional logic may be provided to ensure that the device does not endlessly activate and deactivate the ATP unit despite a chronic lack of success.

Returning to step 302, if a depolarization is detected during the latest escape interval, indicating that some type of intrinsic electrical event occurred, then the stimulation device determines, at step 311, whether the intrinsic event occurred within a period of time at which an intrinsic beat would be expected. More specifically, the overdrive unit compares the timing of the depolarization against a time window representative of an expected intrinsic beat. The time window for the expected intrinsic beat may be calculated in accordance with otherwise routine pacing techniques then, preferably, expanded by 30% in length. In any case, if the depolarization is within the expected range, then the stimulation device interprets the depolarization to be that of a sinus beat and returns to step 300 for detection of the next escape interval. If, however, the depolarization did not occur within the expected time period, the stimulation device concludes that the depolarization is that of a PAC. Assuming PAC response has been enabled (as verified at step 312), a PAC response protocol is initiated, at step 313. Once the PAC response protocol has completed, processing again returns to step 300.

If PAC response has not been enabled within the device then, at step 314, the stimulation device instead waits a period of time, at step 315, to ensure that the heart is no longer refractory (for example 400 milliseconds) and then delivers a pacing pulse, at step 316, at the maximum pulse magnitude. (This maximum pulse magnitude is greater than or equal to the backup pulse magnitude of step 306.) The capture unit attempts to verify capture, at step 318, and if this maximum pacing pulse is properly captured, processing returns to step 300 for calculation of the next escape interval. If, however, the maximum pacing pulse is not captured even though the heart should have been refractory when the pulse was delivered, then AT or AF is presumed and ATP is activated, at step 310.

With respect to the automatic threshold stimulation search performed at step 308, rather than trigger the search based on a single pair of pulses that fail to evoke capture (i.e., a single pacing pulse/backup pulse pair), in alternative implementations the search may instead be triggered based on some number of LOC events occurring within a selected number of pacing cycles. For example, the stimulation threshold search may instead be triggered only if a programmable number of consecutive pacing pulses do not capture or if "x out of y" pacing pulses do not capture (such as if four out of the last seven pulses fail to evoke capture). A technique for exploiting an "x out of Y" approach is set forth in U.S. Pat. No. 6,430,441 to Levine, entitled "Implantable Cardiac Stimulation Device Having Autocapture/Autothreshold Capability," which is incorporated by reference herein.

Thus, FIG. 4 illustrates a technique for automatically activating ATP based on the failure of pacing pulses to properly evoke capture, which seeks to quickly verify that an AT or AF is occurring before activating ATP. With this technique, a single ATP regimen is delivered at step 310 upon detection of AF, then preventive overdrive pacing resumes. Alternatively, the stimulation device may be configured to continuously deliver ATP therapy until AF is terminated or until a predetermined time-out period expires. Also, the ATP unit may be configured to cycle through different types of ATP regimens in an attempt to terminate AF. For example, if a burst ATP technique is not successful during a first execution of step 310, then the next time step 310 is performed the ATP unit may automatically switch to a scanning technique. Also, preventive overdrive pacing need not be performed continuously whenever ATP is not performed. Rather, preventive overdrive pacing may be selectively activated or deactivated and additional logic may be provided for controlling the activation or deactivation of preventive overdrive pacing. In one specific example, preventive overdrive pacing may be deactivated at night or while the patient is asleep to provide for a generally lower sleeping heart rate. If so, otherwise conventional AF detection techniques may be employed while preventive overdrive pacing is deactivated to detect AF for the purposes of triggering ATP. As can be appreciated, FIG. 4 merely provides an overview of technique and numerous and details and alternatives are not shown.

DAO/ATP Setup Procedure

Figure 5:
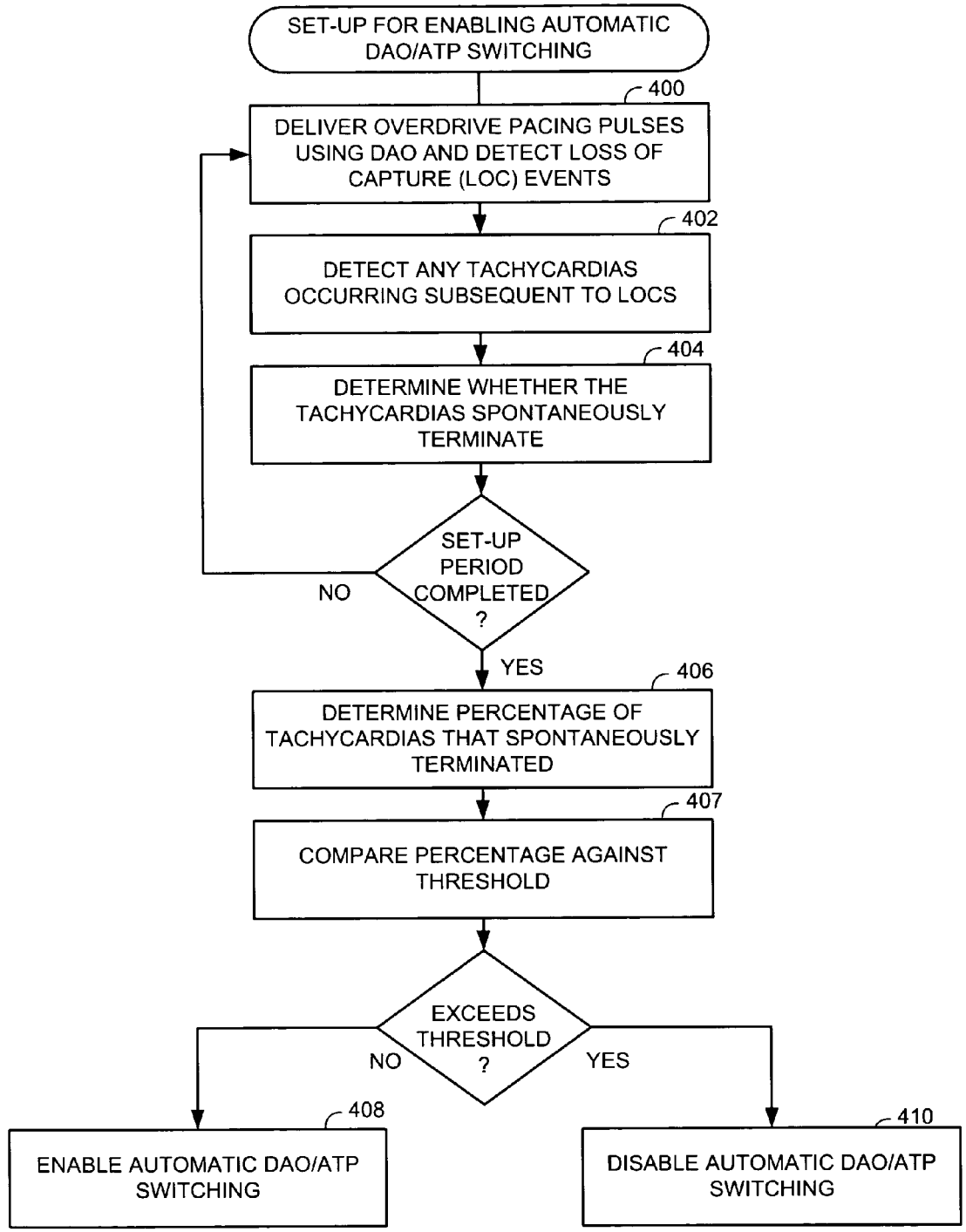
FIG. 5 is a flow chart providing an overview of the operation of yet another exemplary embodiment of the invention and particularly illustrating the manner by which the implantable stimulation device of FIGS. 1 and 2 determines, for a particular patient, whether to enable the automatic switching technique of FIG. 4.

FIG. 5 provides an overview of a set up technique used to determine whether to enable the DAO/ATP switching of the technique of FIG. 4 within the implantable device. The technique is preferably automatically performed following implantation of the device, though the technique can be performed later under the control of a physician via commands entered using an external programmer and transmitted to the implantable device. Briefly, the technique operates to determine whether a tachycardia arising subsequent to LOCs during preventive overdrive pacing spontaneously terminate. If such tachycardias spontaneously terminate, then it is not necessary to activate ATP following LOCs. On the other hand, if most of such tachycardias do not spontaneously terminate, then ATP should be activated as soon as possible following detection of a true LOC during preventive overdrive pacing in an attempt to revert the heart to a normal rhythm.

Beginning at step 400, the microcontroller of the implantable device controls the overdrive pacing unit to deliver preventive overdrive pacing to the heart of the patient while detecting LOCs. Then, the tachycardia detection unit detects any tachycardias arising subsequent to the LOCs, at step 402. Upon detection of a tachycardia, the microcontroller does not activate ATP in an attempt to terminate the tachycardias. Rather, the microcontroller waits a predetermined period of time to determine whether the tachycardia spontaneously terminates. Following completion of a predetermined set up period, which may be, for example, in the range of one to two months (wherein the range is programmable), the microcontroller determines, at step 406, the percentage of tachycardias that spontaneously terminated out of the total number of arrhythmias occurring subsequent to an LOC during preventive overdrive pacing. If the percentage falls below a predetermined threshold, which may be, for example, 60%, then automatic DAO to ATP switching is enabled by the microcontroller, at step 408. Otherwise, automatic switching from DAO to ATP is disabled. Thus, automatic switching from DAO to ATP following detection of an LOC during preventive overdrive pacing is performed only if most tachycardias arising under those conditions do not spontaneously terminate. If most such tachycardias do spontaneously terminate, then automatic DAO to ATP switching is not enabled since most such tachycardias terminate spontaneously and ATP would be unnecessary and, perhaps, counterproductive. Alternatively, rather that repeating steps 400–404 for a predetermined set up period, the steps may be performed until a predetermined number of tachycardia episodes have been detected. The predetermined number may be, e.g., in the range of 10 to 20 episodes. The number of episodes is programmable by the physician and depends, in part, on the particular tachycardias to which a patient may be susceptible, as well as rate, stability, onset, and other criteria. A given patient may have multiple different tachycardias, which would each mandate specific yet different therapies. This will likely impact both the delivered therapies and the likelihood of effectiveness for ATP. In any case, the physician takes these factors into account in determining an appropriate number of episodes to program.

In addition to performing the set up technique of FIG. 5 following implantation of the device, the technique may be periodically performed, perhaps once ever several months, to verify that no changes have occurred within the patient that might affect the percentage of spontaneously terminating arrhythmias and that therefore might affect the determination of whether to enable DAO to ATP switching. Such changes within the patient may arise as a result of new medication regimes or perhaps as a result of the progression or regression of medical conditions within the patient. Progression of congestive heart failure, for example, may increase the percentage of tachycardias that do not spontaneously terminate. Alternatively, the set up technique can be performed under the control of a physician whenever appropriate. Thus, for example, if the physician prescribes new medications to the patient that might affect the spontaneous termination of tachycardias, the physician may wish to control the implantable device to perform the set up process to re-evaluate whether automatic DAO to ATP switching should be activated within the device.

Although not explicitly shown in FIG. 5, at step 404, if the tachycardia has not spontaneously terminated at the end of the time period, ATP is then activated in an attempt to terminate the tachycardia. The predetermined period of time prior to activating ATP may be, for example, in the range of 15–30 seconds. Note that this relatively long delay before triggering ATP is employed only during the set-up procedure—before it is known whether the tachycardias associated with LOC will spontaneously terminate. The relatively long period is provided to give the heart a chance to spontaneously revert to a normal sinus rhythm before ATP is activated. After the set-up procedure has been completed (and if it has been determined that the tachycardias do not spontaneously terminate), then DAO to ATP switching is performed much more quickly in accordance with the techniques described wherein, typically, ATP is activated following a LOC within only two to three seconds.

Also, although described in connection with enabling automatic DAO to ATP switching, the technique of FIG. 5 need not be limited to the use of DAO and may instead employ other types of preventive overdrive pacing. Additionally, although not shown in the figure, diagnostic information pertaining to all episodes of arrhythmia occurring subsequent to an LOC during preventive overdrive pacing is stored within memory for subsequent review by the physician via an external programmer. Thus, the physician can directly review the spontaneous termination percentage detected by the implantable device and can review IEGM signals recorded for the individual episodes of tachycardia. In some circumstances, the physician may wish to override the determination made by the implantable device to, for example, enable automatic switching even though the detected percentage does not exceed the threshold or to disable automatic switching in other cases. Hence, the determination made via the setup technique of FIG. 5 is in no way permanent or dispositive.

Capture Verification of Backup Pulses

As explained above, loss of capture of backup pulses during atrial overdrive pacing may be used to detect an atrial tachycardia so that ATP may promptly be applied. Loss of capture of backup pulses may be used for other purposes as well, such for detecting low amplitude VF based on loss of capture of ventricular backup pulses. Accordingly, FIG. 6 sets forth a general technique for verifying capture of backup pulses, whether atrial or ventricular. Briefly, at step 500, the implanted stimulation device controls the delivery of atrial and/or ventricular pacing pulses to the heart and, at step 502, attempts to verify capture of each pulse using the capture detection unit (item 105 of FIG. 2), which is configured to verify capture of either atrial or ventricular pacing pulses (or both). The pacing pulses may be delivered in accordance with preventive overdrive pacing techniques or in accordance with other pacing techniques. So long as each pulse is captured, pacing continues via steps 500 and 502. If a pulse fails to capture (i.e. a LOC occurs), a backup pulse is delivered at step 504 and the capture detection unit attempts to verify capture of the backup pulse at step 506. If the backup pulse also fails to evoke a response, appropriate action is taken. For example, if the backup pulse was an atrial pulse, then ATP may be delivered at step 508 in accordance with techniques already described. If the backup pulse was a ventricular backup pulse, then defibrillation shocks may be delivered to the heart in accordance with techniques summarized below. However, if the backup pulse was captured, action is taken at step 510 to respond to the original loss of capture of the primary pulse. In particular, stimulation threshold searches may be performed in the atria or ventricles. As already explained, such searches may be triggered based on a single LOC of a primary pulse or may be based on some number of consecutive LOCs or some number of LOCs out of a predetermined number of beats.

Figure 6:
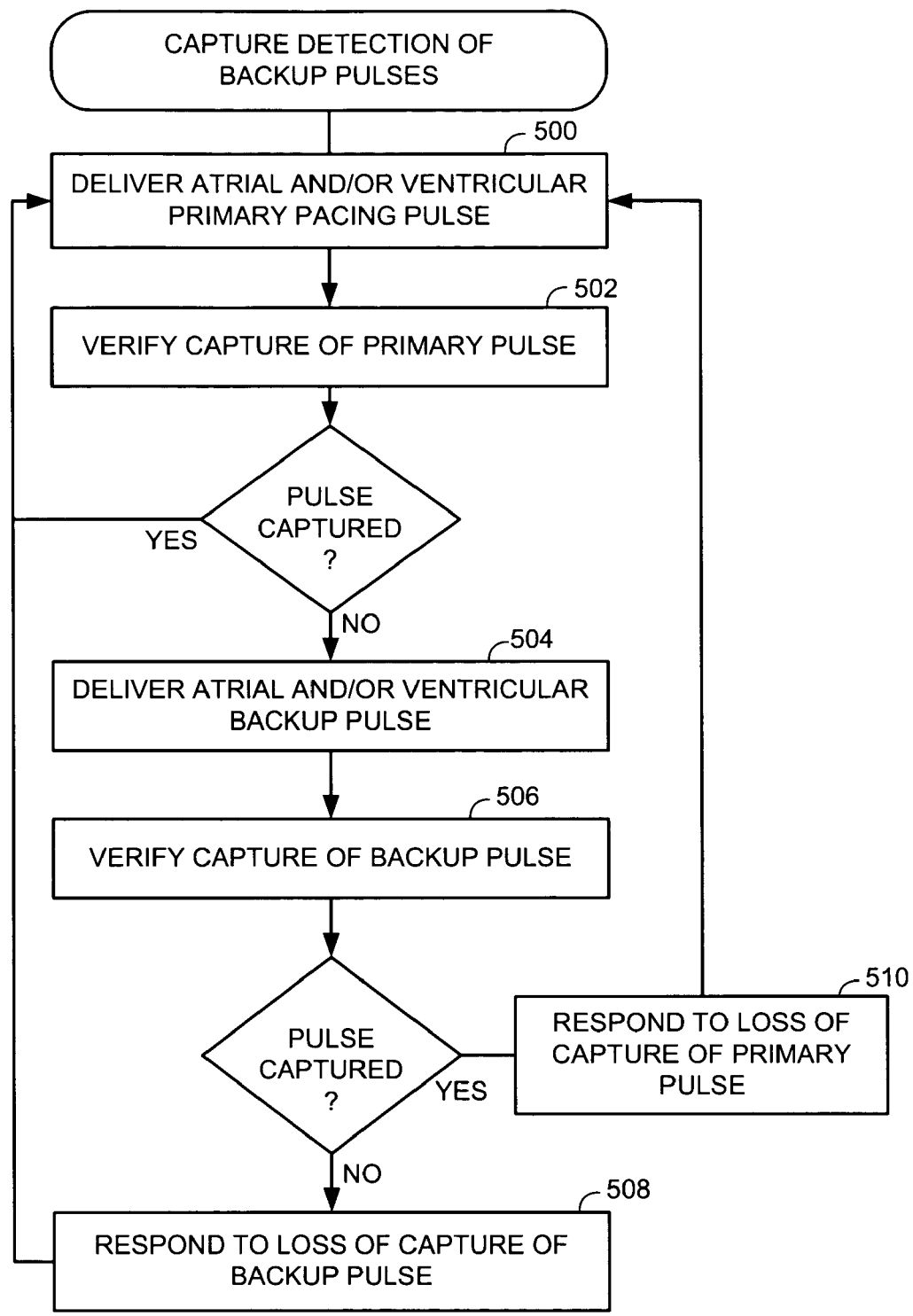
FIG. 6 is a flow chart providing an overview of the manner by which the implantable stimulation device of FIGS. 1 and 2 verifies capture of backup pacing pulses.

Thus, FIG. 6 summarizes a general technique exploiting capture verification of backup pulses. A wide range of specific implementations may be developed in accordance with the general principles of backup pulse capture verification.

Insofar as backup pulses are concerned, see also, U.S. patent application Ser. No. 10/340,099 of Gray, filed Jan. 10, 2003, which provides for measuring the impedance associated with bipolar backup pulses in circumstances wherein a capture threshold has previously been found to have increased. The technique of Gray seeks to detect a possible mechanical problem within the lead but is not directed to capture verification of the backup pulse itself.

Capture-Based Ventricular Tachycardia Detection

Figure 7:
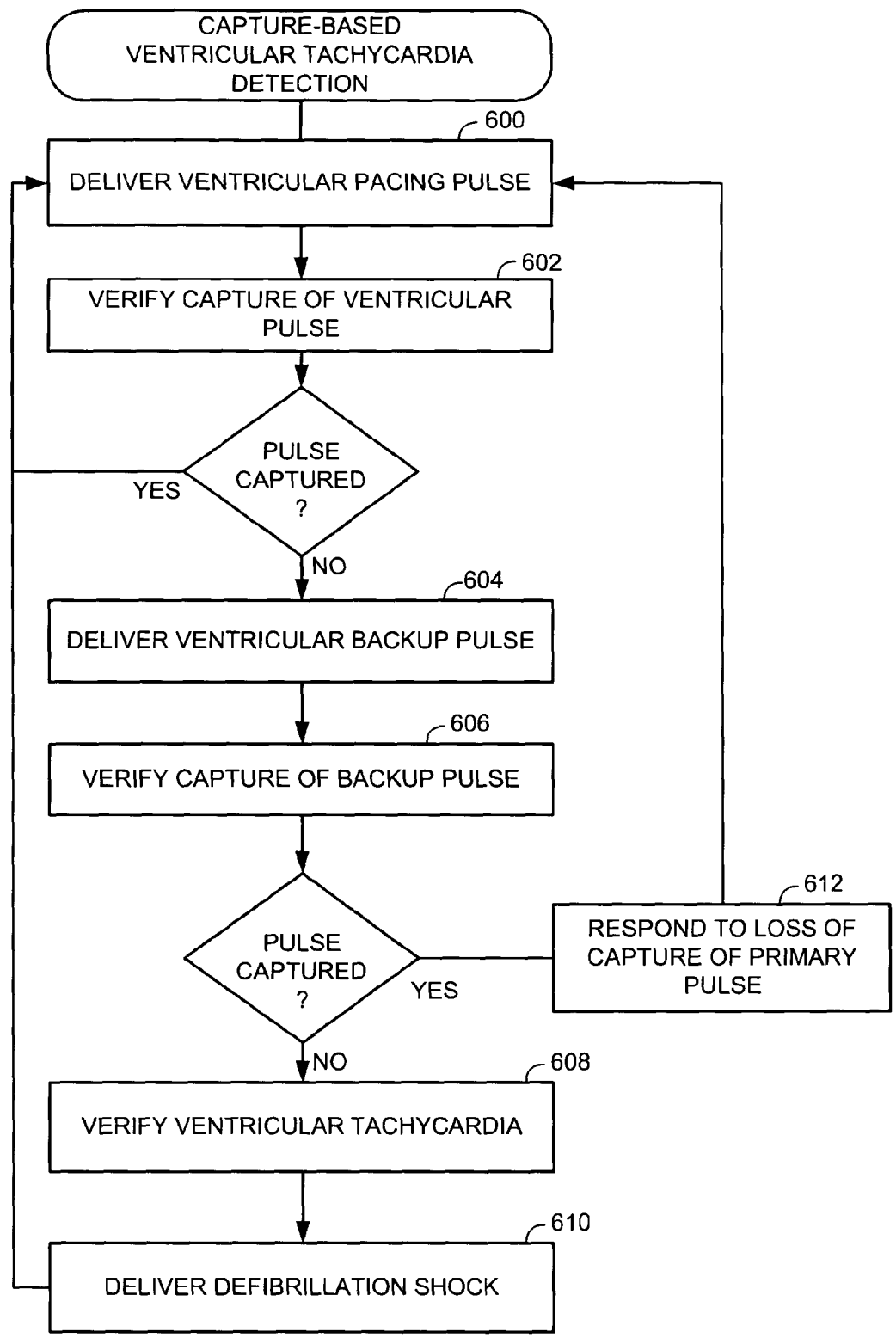
FIG. 7 is a flow chart providing an overview of still yet another of an exemplary embodiment of the invention and particularly illustrating the manner by which the implantable stimulation device of FIGS. 1 and 2 detects ventricular tachycardia based upon loss of capture of ventricular backup pulse.

As noted in the discussions above, ventricular tachycardia may be detected based on loss of capture of ventricular backup pulses. FIG. 7 summarizes this technique. Briefly, at step 600, the implanted stimulation device controls the delivery of ventricular pacing pulses to the heart and, at step 602, attempts to verify capture of each ventricular pulse using the capture detection unit (item 105 of FIG. 2). Depending upon the implementation, the pacing pulses may be delivered in accordance with preventive ventricular overdrive pacing techniques or in accordance with other pacing techniques. So long as each ventricular pulse is captured, ventricular pacing continues via steps 600 and 602. If a ventricular pulse fails to capture, a ventricular backup pulse is delivered at step 604 and the capture detection unit attempts to verify capture of the backup pulse at step 606. If the backup pulse also fails to evoke a response, a possible ventricular tachyarrhythmia is detected, at step 608, such as a low amplitude VF. Steps may then be taken to verify the presence of the VF, such as by increasing a ventricular sensitivity to search for undersensing of ventricular intrinsic events. In any case, if VF is detected, defibrillation shocks are delivered to the heart at step 610. However, if the ventricular backup pulse was captured, action is taken at step 612 to respond to the original loss of capture of the primary ventricular pulse. In particular, a stimulation threshold search may be performed as explained above. As before, such searches may be triggered based on a single LOC of a primary pulse or may be based on some number of consecutive LOCs or some number of LOCs out of a predetermined number of beats.

As can be appreciated a wide variety of techniques can be implemented consistent with the principles the invention and no attempt is made herein to describe all possible capture-based tachycardia detection techniques, DAO/ATP switching techniques, DAO/ATP set up techniques, backup pulse capture detection techniques or ventricular fibrillation detection techniques. Although described primarily with reference to an example wherein the implanted device is a defibrillation/pacer, principles of the invention are applicable to other implanted cardiac stimulation devices as well such as pacemakers without defibrillation capability. The various functional components of the exemplary systems may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. In an implantable cardiac stimulation device having a preventive overdrive pacing unit, a tachycardia detection unit, an antitachycardia pacing (ATP) therapy unit, and a capture detection unit, a method comprising:
    overdrive pacing the heart by delivering overdrive pacing pulses using the preventive overdrive pacing unit;
    detecting loss of capture of pacing pulses during preventive overdrive pacing using the capture detection unit;
    detecting tachycardia occurring subsequent to a loss of capture using the tachycardia detection unit;
    determining, for each tachycardia occurring following a loss of capture, whether the tachycardia spontaneously terminates; and
    selectively enabling automatic switching from preventive overdrive pacing to ATP therapy based on a percentage of spontaneously terminating episodes of tachycardia occurring subsequent to loss capture during preventive overdrive pacing.

2. The method of claim 1 wherein selectively enabling automatic switching from preventive overdrive pacing to ATP therapy comprises:
    comparing the percentage of spontaneously terminating episodes of tachycardia against a predetermined threshold;
    enabling automatic switching from preventive overdrive pacing to ATP therapy if the percentage does not exceed the predetermined threshold; and
    disabling automatic switching from preventive overdrive pacing to ATP therapy if the percentage exceeds the predetermined threshold.

3. The method of claim 2 wherein the predetermined threshold is 60%.

4. The method of claim 1 wherein overdrive pacing the heart, detecting loss of capture of pacing pulses during preventive overdrive pacing, detecting tachycardia occurring subsequent to a loss of capture, and determining, for each tachycardia occurring following a loss of capture, whether the tachycardia spontaneously terminates are performed for a predetermined period of time prior to selectively enabling automatic switching from preventive overdrive pacing to ATP.

5. The method of claim 1 wherein overdrive pacing the heart, detecting loss of capture of pacing pulses during preventive overdrive pacing, detecting tachycardia occurring subsequent to a loss of capture, and determining, for each tachycardia occurring following a loss of capture, whether the tachycardia spontaneously terminates are performed for a predetermined number of tachycardia episodes prior to selectively enabling automatic switching from preventive overdrive pacing to ATP.

6. The method of claim 1 wherein the recited method is performed soon after implantation of the implantable cardiac stimulation device.

7. The method of claim 6 wherein the recited method is performed periodically thereafter.

8. The method of claim 1 wherein the automatic switching from preventive overdrive pacing to ATP therapy comprises:
    delivering overdrive pacing pulses to the heart using the overdrive pacing unit;
    detecting loss of capture of pacing pulses within the heart using the capture detection unit;
    detecting a tachycardia based on the detection of loss of capture of pacing pulses; and
    switching from preventive overdrive pacing to ATP therapy upon detection of the loss of capture.

9. The method of claim 8 wherein delivering overdrive pacing pulses is performed to deliver pulses at a predetermined maximum pulse magnitude and wherein detecting tachycardia is performed by detecting loss of capture of one or more pacing pulses.

10. The method of claim 8 wherein delivering overdrive pacing pulses is performed to deliver pulses at a pulse magnitude less than a predetermined maximum pulse magnitude and wherein detecting tachycardia is performed by detecting loss of capture of both a pacing pulse and a subsequent backup pulse delivered at the maximum pulse magnitude.

11. The method of claim 8 wherein the stimulation device comprises an automatic stimulation threshold search unit operative to determine a capture threshold for pacing pulses and wherein the method further comprises:
    performing a stimulation threshold search using the stimulation threshold search unit if a pacing pulse is not captured during preventive overdrive pacing but a backup pulse is captured.

12. The method of claim 8 wherein delivering overdrive pacing pulses is performed to deliver preventive overdrive pacing to the atria.

13. The method of claim 12 wherein the stimulation device comprises a premature atrial contraction (PAC) detection unit and wherein the method further comprises:
    delivering ATP therapy using the ATP unit upon the detection of a loss of capture of a backup pulse delivered subsequent to detection of a PAC by the PAC detection unit during preventive overdrive pacing.

14. The method of claim 12 wherein the stimulation device includes both a premature atrial contraction (PAC) detection unit and PAC response unit and wherein the method further comprises:
    activating the PAC response unit upon the detection of a PAC by the PAC detection unit during preventive overdrive pacing.

15. In an implantable cardiac stimulation device for implant within a patient, a system comprising:
    an overdrive pacing unit operative to deliver overdrive pacing pulses to the heart for preventing a tachycardia, the overdrive pacing pulses delivered to the heart if no intrinsic depolarization is detected during an overdrive pacing escape interval;
    an antitachycardia pacing (ATP) therapy unit operative to deliver antitachycardia pacing therapy to the heart;
    a capture-based tachycardia detection unit operative to detect a tachycardia based upon loss of capture of overdrive pacing pulses; and
    a control unit operative to control the overdrive pacing unit and the ATP unit and to selectively enable automatic switching from preventive overdrive pacing to ATP therapy based on a percentage of spontaneously terminating episodes of tachycardia occurring subsequent to loss capture during an initial period of preventive overdrive pacing.

16. The system of claim 15 wherein the control unit selectively enables automatic switching from preventive overdrive pacing to ATP therapy by comparing the percentage of spontaneously terminating episodes of tachycardia against a predetermined threshold, enabling automatic switching from preventive overdrive pacing to ATP therapy if the percentage does not exceed the predetermined threshold, and disabling automatic switching from preventive overdrive pacing to ATP therapy if the percentage exceeds the predetermined threshold.

17. The system of claim 16 wherein the predetermined threshold utilized by the control until is 60%.

18. The system of claim 16 wherein the control unit is operative to selectively enable automatic switching from preventive overdrive pacing to ATP therapy following an initial period of preventive overdrive pacing defined by a predetermined period of times.

19. The system of claim 16 wherein the control unit is operative to selectively enable automatic switching from preventive overdrive pacing to ATP therapy following the initial period of preventive overdrive pacing defined by a predetermined number of tachycardia episodes.

* * * * *